United States Patent [19]

Blackburn et al.

[11] Patent Number: 5,763,395
[45] Date of Patent: Jun. 9, 1998

[54] STABILIZED LANTHIONINE BACTERIOCIN COMPOSITIONS

[75] Inventors: Peter Blackburn; Jon de la Harpe, both of New York, N.Y.

[73] Assignee: Ambi Inc., Tarrytown, N.Y.

[21] Appl. No.: 386,122

[22] Filed: Feb. 9, 1995

Related U.S. Application Data

[63] Continuation of Ser. No. 986,671, Dec. 8, 1992, abandoned.

[51] Int. Cl.$^6$ .................................................. A61K 38/16
[52] U.S. Cl. ........................... 514/12; 530/317; 530/324; 530/332; 514/9; 562/559
[58] Field of Search ................................ 562/559; 514/12, 514/9; 530/324, 332, 317

[56] References Cited

U.S. PATENT DOCUMENTS 5,272,135  12/1993  Takruri .......................... 514/12

FOREIGN PATENT DOCUMENTS

| 0431663 | 11/1990 | European Pat. Off. . |
| 8912399 | 6/1989 | WIPO . |
| 9009739 | 2/1990 | WIPO . |
| 9215614 | 9/1992 | WIPO ........................ C07K 15/00 |

OTHER PUBLICATIONS

Lee, et al., "Studies on the antibiotic nisin produced by Streptococcus . . . ", Korean J. Animal Sci. 27: 480–483, 1985.
Chan, Febs Letters 252, 29, 1989.
Barber, Experientia, 44, 266, 1988.
Schechter J Biol Chem 261, 66, 1986.
Schechter J Biol Chem 261, 66–70, 1986.

*Primary Examiner*—David Lukton
*Attorney, Agent, or Firm*—White & Case L.L.P.

[57] ABSTRACT

The invention concerns compositions containing a lanthionine containing bacteriocin such as nisin which are stabilized by the presence of a thioether stabilizing agent against degradation.

15 Claims, 1 Drawing Sheet

STABILIZED LANTHIONINE BACTERIOCIN COMPOSITIONS

This application is a continuation of application Ser. No. 07/986,671, filed Dec. 8, 1992, now abandoned.

BACKGROUND OF THE INVENTION

It is particularly difficult to maintain proteins and peptides stable for extended periods when stored at ambient temperatures, particularly in dilute solution, and this remains a major challenge for formulation chemists. Proteins and peptides can undergo degradation by various pathways, including but not limited to the following:

peptide bond hydrolysis particularly at extremes of pH, deamidation under acidic pH, dehydration and desulfurization at alkaline pH, halogenation of aromatic side chains, oxidation of sulfur-containing and indole side chains, thiol-disulfide rearrangements, modification of amine groups by reactive carbonyl compounds and amadori rearrangements with beta-hydroxy carbonyl compounds, polymerization, precipitation, and denaturation.

The rate of degradation of a protein or peptide can be influenced, by the sequence of adjacent amino acid residues in the molecule; for example Asn-Gly sequences are particularly susceptible to deamidation and beta-rearrangement of the intervening peptide bond. The amino acid sequence, subject to environmental constraints, determines the three-dimensional structure of the molecule which can further influence the rate of degradation of a protein or peptide. The components of a formulation and their interactions can create environmental conditions in the formulation which can influence the structure of a protein or peptide molecule, or they might participate directly in degradative pathways to positively or negatively affect the stability of a protein or peptide in that formulation.

Nisin is a bacteriocin, and in particular, is a member of a family of peptides characterized by the presence of lanthionine-containing ring structures believed to be essential for the integrity and functionality of the molecule. Other members of this class of peptide include, but are not limited to, subtilin, duramycin, cinnamycin, ancovenin, Pep 5, epidermin and gallidermin.

Nisin and its related peptides are antimicrobial agents that, among other things, inhibit the germination and arrest the outgrowth of certain bacterial spores. In this context, a commercial nisin preparation, Nisaplin™ is marketed (Aplin & Barrett, Beaminster, U.K.) as a direct additive in foods to inhibit the growth of certain pathogens and spoilage organisms, in particular thermostable spore forming clostridial species that are responsible for botulism. In addition, nisin and related peptides are active against vegetative forms of certain bacteria responsible for certain diseases in animals and humans.

It has been found that when nisin and related peptide bacteriocins are combined with chelating agents and/or various surfactants,the bactericidal activity of the antimicrobial peptide in such formulations is significantly improved, and is broadened to include a much wider range of bacteria now including species of both gram negative and gram positive bacteria (see U.S. Pat. No. 5,135,910, the disclosure of which is herein incorporated by reference). In addition, the performance of the peptide formulation can be further affected by the presence of various excipients and other carriers useful to facilitate delivery of the formulation to its intended site of action, for example, under physiological conditions for pharmaceutical formulations.

Adequate performance of formulations of nisin and related peptides requires that the peptide remains physically stable and biologically active in the various formulations under conditions of use and storage. Furthermore, the requirements for stability and integrity of active agents, including biologically active peptides, are a subject for regulatory scrutiny.

It has been widely accepted that the activity of lanthionine-containing peptides is relatively stable and can even tolerate extreme temperatures. The nisin preparation, Nisaplin™, has been used under extreme temperatures, for example during pasteurization and even at the retort temperatures used in canning of certain foods. Despite this apparent stability it has been found that upon storage these bacteriocin molecules undergo degradative changes some of which, but not all, result in a loss of bioactivity. It has been shown by Chan et al. "Isolation and characterization of two degradation products derived from the peptide antibiotic nisin," FEBS Letters, Vol. 252 No. 1,2, 29–36 (July 1989) that upon storage of the spray-dried preparation Nisaplin™, nisin in the preparation undergoes degradation with the accumulation of breakdown products separable by reversed phase high performance liquid chromatography (RPHPLC) on silica based resins eluted with gradients of organic modifier.

Compounds as widely diverse as proteins (e.g., albumin), amino acids, surfactants, alcohols, carbohydrates and various oxygen and radical scavengers have been cited as candidates for the stabilization of peptides and proteins in solution. While nisin alone in dilute acid or a buffered solution in the pH range 2 to 5 shows good stability characteristics, it has been found that some substances such as certain emulsifiers and surfactants which enhance the bactericidal activity of lanthionine-containing bacteriocins in formulations (see U.S. Pat. No. 5,135,910) may also accelerate the degradation of the bacteriocins over the course of time.

Many commonly used stabilizers and antioxidants are virtually ineffective in overcoming the degradation of lanthionine-containing peptides. Consequently new agents were sought which would counteract the degradation of the bacteriocins in the formulation and which would thus yield compositions of enhanced and stable shelf life.

SUMMARY OF THE INVENTION

The present invention concerns compositions comprising lanthionine-containing peptide bacteriocins such as nisin stabilized by the presence of a suitable thioether compound as a stabilizer. The thioether compound is preferably a compound of the formula I.

$$R^1—S—R^2 \qquad (I)$$

wherein $R^1$ is an alkyl group containing 1–6 carbon atoms or $$—(CH_2)_n—CH—COOH$$
$$\qquad\quad |$$
$$\qquad\quad NH_2$$

and $R^2$ is $$—(CH_2)_n—CH—R^4$$
$$\qquad\quad |$$
$$\qquad\quad R^3$$

wherein n is 0 to 5; $R^3$ is hydrogen an amino group, or an hydroxyl group; and $R^4$ is a hydrogen, a carboxyl group, an ester group or an amido group wherein the amino function is contributed by an amino acid residue or wherein $R^1$ and $R^2$ together are joined to form, with the sulfur, a thiazolidine ring.

In a preferred embodiment, the compound of formula I is the amino acid methionine or an analog thereof.

The present invention further concerns methods of stabilizing nisin and other lanthionine-containing peptides in solution and in dry mixtures. According to the invention, a compound of formula I is added to a composition comprising a lanthionine-containing peptide bacteriocin in an amount sufficient to protect the lanthionine containing bacteriocin from degradation. The stabilizer compound may be added to lanthionine bacteriocin upon formulation or alternatively it may be pre-formulated with one or more of the non-bacteriocin components prior to formulation with the bacteriocin.

The addition of a compound of formula I, which is preferably methionine or an analog thereof, stabilizes the active bacteriocin ingredient over a broad pH range and does not compromise in any way the potency or utility of the compositions.

DETAILED DESCRIPTION OF THE INVENTION:

Lanthionine-containing bacteriocins such as nisin can be formulated into a variety of compositions which exhibit bactericidal activity against gram-negative and gram-positive organisms. These bacteriocin compositions which, in addition to the bacteriocin also may contain surfactants, emulsifiers, chelating agents, humectants and other excipients such as thickening agents, flavors, fragrances, abrasives and lubricants, are used in a wide variety of applications such as oral rinses, topical disinfectants, pharmaceutical compositions, dentrifices, disinfectant paper wipes, food preservatives, germicides, intramammory infusions, etc. Such composition and methods for preparing them are described in U.S. Pat. No. 5,135,910, whose disclosure is herein incorporated by reference.

The lanthionine containing bacteriocins used in these bactericidal compositions can be selected from the group consisting of, nisin, subtilin, duramycin, cinnamycin, ancovenin, Pep 5, epidermin, and gallidermin. While the lanthionine bacteriocin is not limited to the selection of the above group, the preferred bacteriocin is nisin.

Suitable surfactants used in combination with lanthionine containing bacteriocins in such bactericidal compositions are: polyethoxylated sorbitol esters, e.g., Peg(40) sorbitan diisostearate, Tweens™; polycondensates of ethylene oxide and propylene oxide, e.g., Poloxamers, Pluronic, F127, F68; polyethoxylated hydrogenated castor oil, e.g., Cremophor, El, RH40; sorbitan fatty esters; long chain imidazoline derivatives, e.g., Miranol C2M; long chain alkyl betaines, e.g., Empigon BB; long chain alkyl amidoalkyl betaines, e.g., cocamidopropylbetaine; D, L-2-pyrrolidone-5-carboxylic acid salt of ethyl-N-cocyl-L-arginate, e.g., CAE; cocamidopropyl PG diammonium chloride, EGM Monoquat PTC; lauramidopropyl, e.g., Monaquat BTL; Tagat, R60, L2, 02, S2; Cetiol HE; Pyroter; Ryoto sugar; Tensopol; Tegobetaine; Incromine; Solutol HS15 and laurainine oxide.

The instant invention provides compositions, and methods for producing the same, which are improved over previously disclosed compositions comprising lanthionine containing bacteriocins. The inventive compositions not only act as enhanced broad range bactericides but in addition, have an extended shelf life greater than that of the prior art compositions. The inventive bacteriocin compositions containing a suitable thioether stabilizing agent may be formulated into solutions or dry compositions such as freeze dried preparations.

Representative Formulations Comprising Lanthionine-Containing Bacteriocins

Bactericidal formulations for use in the present invention may be formulated as disclosed in U.S. Pat. No. 5,135,910. In addition, these formulations may be stabilized by the addition of suitable thioether compounds as disclosed herein and for specific application excipients may be added to the formulation suited to the purposes of the commercial application. Representative formulations and ingredients are set forth below. The concentration and inclusion of the excipients may be varied by those of ordinary skill in the art so as to obtain the preferred properties desired for each formulation.

(i) A nisin-containing formulation useful as an oral rinse or dentrifice comprising:

ethanol or other alchohols poloxamer, polysorbate or other emulsifiers/surfactants EDTA, citrate or other chelator coolmint or other flavors glycerol, propylene glycol or other humectants blue dye or other colors saccharin or other sweeteners nisin or other lanthionine containing bacteriocins May also contain thickeners such as hydroxyethyl cellulose and abrasives such as silica or diatomaceous earth for use as a dentrifice. May contain xanthan gums or stearate salts useful for formulating as a tablet.

(ii) A nisin-containing formulation useful as a topical germicide comprising:

1-propanol, ethanol or other alchohols polysorbate or other emulsifier/surfactants propylene glycol, glycerol or other humectants EDTA, citrate or other chelators nisin or other lanthionine-containing bacteriocins water qs May also contain thickeners such as polyvinylpyrrolidone, hydroxyethyl cellulose, alginates or silicones. In addition may contain fragrances.

(iii) A nisin-containing formulation useful as a deodorant comprising:

1-propanol, ethanol or other alchohols polysorbate or other emulsifier/surfactants propylene glycol, glycerol or other humectants EDTA, citrate or other chelators fragrances nisin or other lanthionine-containing bacteriocins water qs (iv) A nisin-containing formulation useful as an intramammary infusion for treating mastitis comprising:

polysorbate or other emulsifier/surfactants

EDTA, citrate or other chelators glycerol, sorbitol, propylene glycol or other humectants
nisin or other lanthionine-containing bacteriocins
water qs

Thioether Stabilizing Compounds

The inventive thioether stabilizing agents are effective in increasing the stability of bacteriocins such as nisin when formulated with a wide range of surfactants, chelators, emulsifiers and humectants. While different components exhibit different degrees of associated degradation, the addition of the inventive thioether stabilizing agents is expected to have a beneficial effect in all situations in which a lanthionine containing bacteriocin is formulated with such components. The thioether stabilizing agents also increase the stability of nisin in a wide variety of formulations with chelating agents in combination with the humectants glycerol or sorbitol.

According to the invention, the lanthionine-containing peptide compositions typically would have a peptide concentration in the range of 1 µg/ml to 1000 µg/ml, preferably in the range of 30 µg/ml to 300 µg/ml, a surfactant-t concentration in the range of 0.1% to 10.0% and a concentration of a thioether stabilizer compound in the range of 1 mM to 50 mM. In most instances, a stabilizer concentration in the range of 1 to 10 mM will be sufficient to maintain the initial potency of the active ingredient.

While any suitable thioether stabilizer compound may be used as a stabilizer for these bacteriocin formulations it is preferred that the stabilizing compounds of the formula I below be used:

$$R^1—S—R^2 \qquad (I)$$

wherein $R^1$ is an alkyl group containing 1–6 carbon atoms or and $R^2$ is wherein n is 0 to 5; $R^3$ is hydrogen, an amino group, or an hydroxyl group; and $R^4$ is a hydrogen, a carboxyl group, an ester group or an amido group wherein the amino function is contributed by an amino acid residue or wherein $R^1$ and $R^2$ together are joined to form, with the sulfur, a thiazolidine ring.

Preferably the compound of formula I is methionine, an analog thereof, or a related thioether compound. Suitable compounds for use in the invention are methionine, methionine hydroxy analog, methionine methyl ester, methionine ethyl ester, thiazolidine, and lanthionine. In certain embodiments of the invention the thioether stabilizing compound may be a peptide or a polymer rich in methionine, or methionine analog residues. Methionine hydroxy analog, or MHA, is the compound 2-hydroxy-4-(methylthio)butanoic acid.

According to further embodiments of the invention, the thioether stabilizing agent may be defined by the formula II described below:

$$R^1—S—R^2 \qquad II$$

wherein $R^1$ is an alkyl group containing 1–6 carbon atoms or n is 0–5
wherein $R^3$ is hydrogen or x is 1–3; and $R^4$ may be —H, —CH$_3$, —CH(CH$_3$)$_2$, —CH$_2$CH(CH$_3$)$_2$, —CH(CH$_3$)CH$_2$CH$_3$, —CH$_2$SH, —CH$_2$CH$_2$SCH$_3$, —CH$_2$OH, —CH(OH)CH$_3$, —CH$_2$COOH, —(CH$_2$)$_2$COOH, —CH$_2$CONH$_2$, —(CH$_2$)$_2$CONH$_2$, —(CH$_2$)$_4$NH$_2$, or —(CH$_2$)$_3$— joined with the amino group of $R^3$ to form a pyrrolidine ring; and
$R^2$ is wherein $R^5$ is hydrogen, an amino group or a hydroxyl group and $R^6$ is hydrogen or wherein $R^7$ is hydroxy, alkoxy containing 1–6 carbon atoms or and n, x and $R^4$ are as defined above.

The thioether stabilizing compound must also be suitable for the intended use of the formulation. Some thioether stabilizing compounds may protect against nisin degradation, however the usefulness of such compounds may be limited because of their odor, toxicity or carcinogenicity. Thus, the thioether stabilizer compounds must also be selected so that they are suitable for the specific commercial application and so that they do not possess adverse characteristics which cannot be remedied.

The examples set forth below demonstrate that the thioether stabilizing compounds of the invention and preferably the compounds of formula I, e.g. methionine and related compounds, are effective, while commonly used antioxidants are not, in stabilizing lanthionine-containing peptides against degradation associated with surfactant, chelating agent or humectant components of the compositions. The data indicate that the stabilizing agents not only preserve the physical integrity but also do not interfere with the biological properties of the active-ingredient peptides.

Methods of Determining Nisin Stability

The stability of nisin may be determined in a number of ways. Those used in the examples in this application were: (i) analytical reverse phase high pressure liquid chromatography and (ii) the Minimum Inhibitory Concentration Assay described below:

i) Analytical reverse phase high pressure liquid chromatography (RPHPLC). The analyte (nisin) in solution is passed through a column of hydrophic beads to which the nisin tends to bind. The solution flowing through the column is then made progressively more hydrophobic by increasing acetonitrile concentration until it causes the nisin to be released from the beads and eluted from the column. The emergence of the nisin from the column is detected by measuring the absorbance of light at 210 nm by the effluent.

A second detection system may also be used in conjunction with RPHPLC, by reacting amine-containing components emerging from the column with fluorescamine. The products of this reaction are fluorescent and may be detected by an appropriate monitor. The advantage of the fluorescence-based system is that it is sensitive only to amine-containing analytes (nisin has four amine groups). This allows the analysis of nisin in complex formulations where other components interfere with the detection of nisin by absorption at 210 nm.

ii) Estimation of the minimum inhibitory concentration (MIC) of the nisin solution. This measures the functional activity of the nisin in the solution by testing its ability to kill or prevent the growth of a target bacterial population.

A series of two-fold dilutions of the solution of nisin to be tested is prepared. Aliquots of 5 μl of these solutions are pipetted onto a lawn of target bacteria (*Staphylococcus aureus*) growing on a gel of nutrient agar in a petri dish. The dish is covered and incubated at 37° C. overnight (~16 hr). Where the nisin concentration is sufficiently high to prevent growth of the bacteria there is a zone of clearance in the bacterial lawn. The activity of a nisin solution being tested is given as the lowest nisin concentration inhibiting the growth of the bacteria (the minimum inhibitory concentration).

EXAMPLE 1

Oral rinse formulations containing nisin were formulated with a variety of alternative components to determine which component(s) was associated with the degradation of the nisin. A series of formulations was prepared in which each component was omitted in turn. These formulations and their components are set forth in Table 1. Residual nisin concentration is shown in μg/ml. The initial nisin concentration was 300 μg/ml.

A reference solution of nisin in 10 mM HCl was prepared as well as a full formulation with no omissions. After incubation at room temperature for 3 days the formulations were analyzed by RPHPLC to determine the extent of degradation of the nisin.

TABLE 1

Residual Nisin Concentration In An Oral Rinse With Sequential Component Omission

| | Component omitted | Nisin (μg/ml) | % Theoretical conc. |
|---|---|---|---|
| nisin standard | | 300 | 100 |
| full formulation | | 206 | 69 |
| | color FD&C Blue No. 1 | 189 | 63 |
| | | 223 | 74 |
| | glycerol | 154 | 51 |
| | ethanol | 163 | 54 |
| | saccharin | 149 | 50 |
| | EDTA | 274 | 91 |
| | polysorbate | 146 | 49 |
| | Poloxamer 407 | 154 | 51 |
| | flavor - coolmint (Noville) | | |

Examination of the RPHPLC chromatograms for the formulations of Table 1 revealed that all the formulations showed accelerated nisin degradation relative to the reference in 10 mM HCl but that degradation was minimized in the formulations in which the polysorbate surfactant/emulsifier or the glycerol humectant were omitted.

Formulations of nisin useful as oral rinses comprising EDTA and the humectant glycerol were also prepared and analyzed by RPHPLC. These studies revealed a source of nisin degradation which was dependent on the simultaneous presence of both EDTA and glycerol in the formulation. Neither compound caused a problem in the absence of the other.

Glycerol and sorbitol from a number of sources, and a number of alternative chelators, were screened (Tables 2 and 3). No source of glycerol nor of sorbitol was found which was without effect on nisin stability in these formulations, and none of the chelating agents tested eliminated the problem, although citrate was superior to EDTA.

TABLE 2

Glycerol And Sorbitol Batches Screened For Effects On Nisin Stability

| | |
|---|---|
| Dow Glycerol | |
| P&G glycerol batches | #925-371, #925-647, #925-602 |
| Henkel glycerol batches | #ODG14, #OGG06, #OGG07 |
| Witco glycerol batches | #OU4314, #OR2245, #9X5951 |
| Pfizer sorbitol batches | #GO6150, #GO6200, #GO6270 |
| Roauette sorbitol batches | #4878, #4710, #4929 |

TABLE 3

Chelating Agents Screened For Effects On Nisin Stability

| | |
|---|---|
| EDTA | (ethylenediaminetetraacetic acid) |
| EGTA | (ethyleneglycol-bis-(β-aminoethyl ether) N,N,N',N'-tetraacetic acid) |
| CDTA | (1,2-diaminocyclohexane N,N,N',N'-tetraacetic acid) |
| DTPA | (diethylaminetriaminepentaacetic acid) |

TABLE 3-continued

Chelating Agents Screened For Effects On Nisin Stability

| | |
|---|---|
| HEEDTA | (N-hydroxyethylethylenediaminetriactic acid) |
| EDITEMPA | (N,N,N',N'-ethylenediaminetetra(methylenephosphonic acid)) |
| citrate | |

EXAMPLE 2

In order to further analyze the nisin degradation associated with one particular surfactant/emulsifier, polysorbate, material was obtained from as many manufacturers as possible. Where possible, multiple production batches were obtained from each manufacturer. Other emulsifiers or surfactants believed to closely resemble polysorbate in their properties as well as dissimilar surfactants were also tested. An oral rinse formulation containing nisin was prepared using each of these compounds and, after incubation, samples were analyzed to evaluate nisin stability. The manufacturers and multiple batches of components tested are listed in Table 4.

TABLE 4

Manufacturers And Batches Of Polysorbate Or Similar Surfactants Tested For Use In Nisin Formulations.

| | |
|---|---|
| Lonza Polysorbate | |
| Heterene Hetsorb L20 P lots | #18142, #20716, #18410, #18546 |
| Mazer T-MAZ 20 lots | #79779, #109104, #105665, #83371, #98372, #96864, #95338, #95523, #82240, #80777 |
| Crdoa Crillet 1 lots | #WB1181, #WB1651DU, #WB1333DU |
| ICI Tween 20, 40, 60, 65, 80, and 85 | |
| ICI Arlatone B | |
| ICI Arlatone G | |
| ICI Arlatone T | |
| ICI Arlacel 165 | |
| ICI Arlasolve 200 | |

Great variation was observed in nisin stability in the presence of the emulsifier/surfactants obtained from different manufacturers; nisin stability was even markedly different using different batches of the same product. However, it was significant that all of the surfactants on the extensive list tested, accelerated nisin degradation to some extent, relative to control formulations in which the emulsifier/surfactant was omitted.

One possible explanation for this degradation may be the introduction of substances during the manufacturing process of formulation excipients. For example, to enhance the appearance of polysorbate the product is bleached by addition of peroxide, a well known oxidizing agent. It seemed quite possible that the presence of residual peroxide in polysorbate contributed to nisin instability. Nisin was found to rapidly degrade on exposure to peroxide (Table 5). Nisin was partially protected by the presence of EDTA. An assay for peroxide was used to screen the various batches of polysorbate used in nisin formulations described herein, but no relationship could be seen between residual peroxide levels and nisin stability. Furthermore, samples taken from a production batch at Mazer Chemicals immediately prior to and immediately after the bleaching step were found to be equivalent in their effects on nisin stability. Thus peroxide added during manufacture may likely not be the agent of degradation.

TABLE 5

Residual nisin concentration (μg/ml) after 8 days at room temp. Initial nisin concentration was 300 μg/ml.

| | peroxide (μM) | | | | glyceraldhyde Z(μM) | | |
|---|---|---|---|---|---|---|---|
| | 100 | 10 | 1 | 0 | 1000 | 1000 | 10 |
| NaOAC, Fe, peroxide | 86 | 261 | 280 | 294 | | | |
| EDTA, Fe, peroxide | 170 | 273 | 297 | 303 | | | |
| NaOAC, peroxide | 154 | 263 | 289 | 283 | | | |
| EDTA, peroxide | 175 | 284 | 295 | | | | |
| NaOAC, glyceraldehyde | | | | | 257 | 291 | 290 |
| EDTA, glyceraldehyde | | | | | 273 | 289 | 285 |

EXAMPLE 3

A number of commonly used antioxidants were tested for their ability to protect nisin in formulation using the methods described in Example 2. The compounds and combinations tested are listed in Table 6. None of the compounds tested gave satisfactory protection of nisin. In fact some compounds in the list aggravated the stability problem, e.g., dithiothreitol (DTT), ascorbate, sodium sulfite.

TABLE 6

Commonly Used Antioxidants Tested For Protection Of Nisin In Formulation.

butylated hydroxytoluene (BHT)
butylated hydroxyanisole (BHA)
propyl gallate
alpha-tocopherol
phenylene-diamine
ethoxyquin
ascorbic acid
citric acid
hydroquinone
dithiothreitol (DTT)
sodium sulfite
BHA + BHT + propyl gallol + citric acid
imidazole
sodium thiosulfate
sodium benzoate

EXAMPLE 4

The stabilization of nisin at 25 μg/ml by a range of sulfur-containing compounds was evaluated in formulations useful as topical germicides comprising polysorbate (T-MAZ 20, Mazer Chemicals) with propyleneglycol, 1-propanol, and either EDTA or citrate. In order to expedite the execution of these experiments the formulations were subjected to "stressed" conditions, ie pH 6 and 40° C.; both intended to accelerate any degradation effects taking place. The stability of nisin in the formulations was evaluated by RPHPLC. The data in Tables 7, 8 and 9 illustrate that the thioether compounds, L- and DL-methionine, DL-methionine methyl or ethyl esters, and DL-methionine hydroxy analogue are all able to stabilize nisin from degradation. To a lesser degree, nisin was also stabilized by the thioether compounds thiazolidine and lanthionine. The disulfide compounds cystine and oxidized glutathione, cysteic acid, methionine sulfoxide and methionine sulfone, and the sulfhydryl compound cysteine did not stabilize nisin from degradation. In addition, the dibasic amino acid lysine did not stabilize nisin.

The stabilization of nisin by methionine in formulations useful as topical germicides where other emulsifier/surfactants were substituted for polysorbate was tested. Formulations were prepared with nisin at 25 µg/ml and titrated to pH 6. They were incubated at 40° C. for 3 days and then analyzed by RPHPLC. The data in Table 10 illustrates that methionine also enhances nisin stability in formulations containing Brij, Tergitol, Tyloxapol, and Triton.

TABLE 7

Residual nisin concentration as a percentage of the theoretical concentration after 5 days at 40° C., pH 6

| jd6-35-H | T-MAZ 20 Batch # | EDTA (mM) | Citrate % | control | Met (1 mM) | Lys (1 mM) | CySH (1 mM) |
|---|---|---|---|---|---|---|---|
| standard | | | | 100 | | | |
| 33–36 | 357 | 1 | | 87 | 84 | 80 | 85 |
| 37–40 | 357 | | 0.1 | 73 | 75 | 71 | 29 |
| 41–44 | 357 | | 0.3 | 71 | 76 | 71 | 36 |
| 45–48 | 357 | | 1.0 | 67 | 73 | 71 | 31 |
| 49–52 | 348 | 1 | | 55 | 80 | 56 | 51 |
| 53–56 | 348 | | 0.1 | 49 | 76 | 45 | 36 |
| 57–60 | 348 | | 0.3 | 49 | 73 | 47 | 29 |
| 61–64 | 348 | | 1.0 | 51 | 73 | 49 | 33 |

Met = methionine; Lys = lysine; CySH = cysteine

TABLE 8

Residual nisin concentration after incubation for 2 weeks at 40° C. Nisin Concentration (µg/ml)**

| | T-MAZ 20 BATCH 357 | T-MAZ 20 BATCH 348 |
|---|---|---|
| water control | 19.5 | 9.5 |
| methionine | 23.2 | 23.3 |
| MHA | 22.5 | 23.4 |
| cystine* | 11.1 | 9.0 |
| cysteic acid | 19.5 | 9.6 |
| glutathione (oxidized) | 14.1 | 7.6 |
| lanthionine | 18.2 | 10.7 |
| thizaolidine | 17.3 | 14.9 |

*Cystine at 5 mM came out of solution as the pH was raised to 3.5.
**Nisin was formulated at 25 µg/ml.

TABLE 9

Residual nisin concentration (µg/ml) after 6 days at 40° C.

| Stabilizer | nisin (µg/ml) | T-MAZ 20 % |
|---|---|---|
| no methionine | 10.1 | 1 |
| DL-methionine | 19.7 | 1 |
| L-methionine | 19.9 | 1 |
| DL-methionine methyl ester | 21.9 | 1 |
| DL-methionine methyl ester | 20.8 | 1 |
| DL-methionine sulfoxide | 8.6 | 1 |
| DL-methionine sulfone | 8.6 | 1 |
| methionine hydroxy analog (Sigma) | 18.1 | 1 |
| methionine hydroxy analog (MHA Novus) | 19.8 | 1 |
| no stabilizer, no T-MAZ-20 | 21.8 | 0 |

*The initial concentration of nisin was 25 µg/ml.

TABLE 10

Stabilizing effect of methionine on nisin at 25 µg/ml in a dermatological formulation under stressed conditions. Formulations were prepared at pH 6.0, substituting other surfactant agents for polysorbate (T-MAZ 20). Formulations were incubated for 3 days at 40° C. to accelerate the degradation of nisin.

| surfactant | no methionine | 5 mM methionine |
|---|---|---|
| T-MAZ 20 | 16.9 | 20.5 |
| Brij | 7.2 | 12.7 |
| deoxycholic acid | 20.0 | 20.3 |
| Tergitol | 3.8 | 9.7 |
| Tyloxapol | 10.0 | 19.4 |
| Triton X-305 | 17.1 | 20.2 |
| Triton X-100 | 8.9 | 12.1 |

EXAMPLE 5

Figure 1:
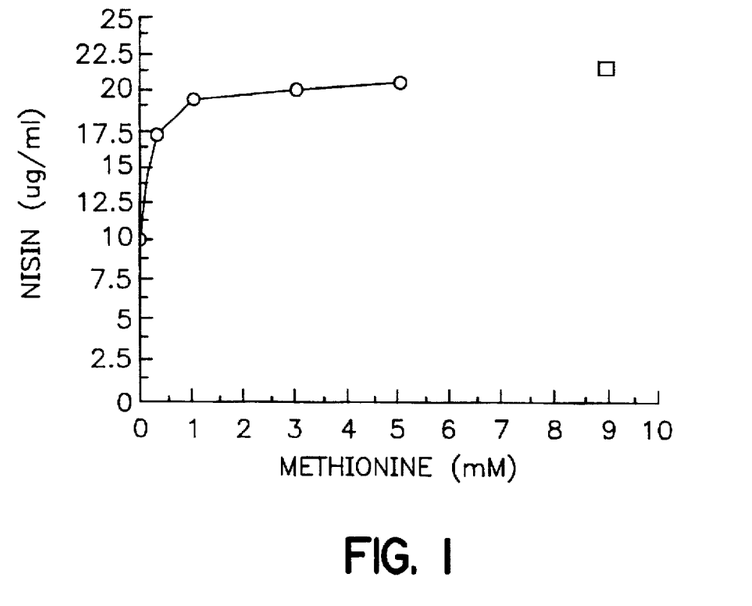
FIG. 1 shows the effect of different concentrations of methionine on the stabilization of nisin in the presence of the polysorbate surfactant T-MAZ 20 at pH 6.

A series of tests was performed to determine the methionine concentration required for stabilization of nisin in a topical germicide formulation containing the polysorbate surfactant, T-MAZ 20, with methionine at concentrations in the range 0 to 5 mM. The stability of nisin in these formulations was compared to that of nisin in a formulation in which the polysorbate was omitted (FIG. 1).

Figure 2:
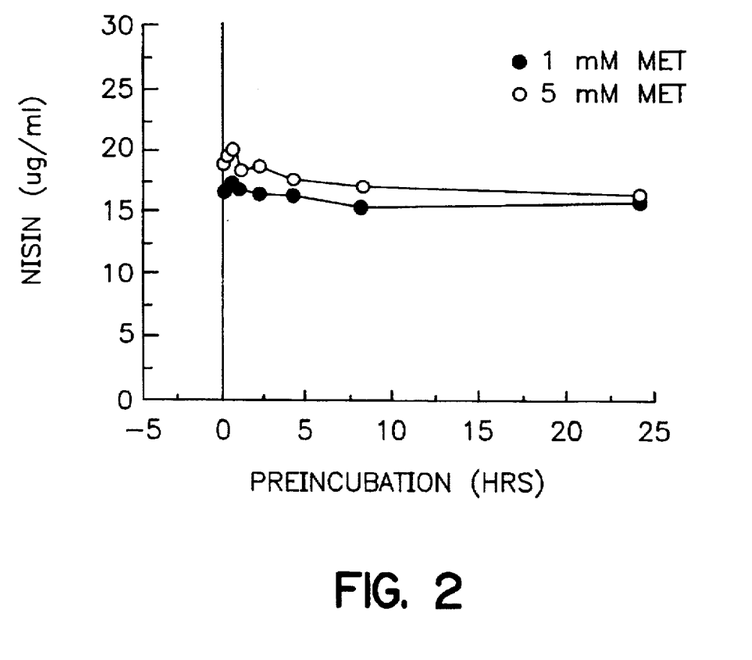
FIG. 2 shows the stability of nisin formulated with polysorbate (T-MAZ 20) preincubated with methionine.

A topical germicide formulation containing nisin was also prepared using the polysorbate T-MAZ 20 preincubated for the indicated times as a 10% solution containing methionine at 10 mM or 50 mM. Various preincubation mixtures were prepared and subjected to different preincubation time periods. Following preincubation, the treated mixture was diluted ten-fold when combined with nisin, resulting in a composition 1% in T-MAZ 20 and either 1 mM or 5 mM in methionine. The samples were then incubated at 40° C. for 12 days and subsequently analyzed for nisin by RPHPLC. The results are shown in FIG. 2. While there appears to be no advantage imparted to stabilization by preincubation, such a preincubation component manufacturing process may offer other advantages in terms of manufacturing efficiency, etc.

EXAMPLE 6

A stabilized nisin formulation useful as an oral rinse was prepared as in Example 1 comprising a) polysorbate, b) glycerol or sorbitol, c) EDTA or citrate, and d) methionine in the concentrations as indicated in Table 11 below.

The formulations were adjusted to pH 4.0 and stored at 40° C. After 1 month samples were analyzed by RPHPLC. The estimated nisin concentration is shown in Table 11. Initial nisin concentration in the formulations was 100 µg/ml.

TABLE 11

| 10% Humectant | EDTA (mM) | citrate (%) | methionine (mM) | Nisin (µg/ml) |
|---|---|---|---|---|
| sorbitol | 1 | | 0 | 88.9 |
| sorbitol | 1 | | 1 | 94.1 |
| sorbitol | 1 | | 2 | 97.7 |
| glycerol | 1 | | 2 | 94.8 |
| glycerol | | 0.3 | 2 | 84.9 |

Residual nisin concentrations in oral rinse formulations.

EXAMPLE 7

A stabilized nisin formulation useful as a deodorant was prepared using polysorbate T-MAZ 20 at pH 3.5, incubated for three (3) months at 40° C., and analyzed by RPHPLC after 3 months. The results are presented in Table 12.

TABLE 12

Residual nisin concentration in deodorant formulations at pH 3.5.

| Sample No. | Ethanol % | Tween 1% Batch # | Met 1 mM | Nisin* (µg/ml) |
|---|---|---|---|---|
| 1 | 35 | 357 | | 4.2 |
| 2 | 35 | 357 | + | 22.4 |
| 3 | 35 | 348 | | 8.8 |
| 4 | 35 | 348 | + | 21.7 |
| 5 | 35 | — | | 9.3 |
| 6 | 35 | — | + | 24.4 |

*Initial Nisin concentration was 25 mg/ml. Nisin concentrations were determined by RPHPLC.

Deodorant formulations were also prepared with polysorbate T-MAZ 20 and methionine at 0, 1, 3, or 5 mM. Formulations were titrated to pH 3.5, 4.5, or 6.0 and set to incubate at 40° C. Samples were analyzed by RPHPLC after 5 days, 13 days, and 60 days. The estimated residual nisin concentration is shown in Table 13 below.

TABLE 13

Residual Nisin Concentration in Deodorant Formulations at a Range of pH 3.5 to 6.0.

| | pH 3.5 | | | pH 4.5 | | | pH 6.0 | | |
|---|---|---|---|---|---|---|---|---|---|
| | days: | | | | | | | | |
| Met* (mM) | 5 | 18 | 60 | 5 | 18 | 60 | 5 | 22 | 60 |
| | Nisin Concentration µg/ml* | | | | | | | | |
| 0 | 21.3 | 16.6 | 10.7 | 21.2 | 14.1 | 3.9 | 20.1 | 10.3 | 3.3 |
| 1 | 23.7 | 21.7 | 16.2 | 22.7 | 21.6 | 13.4 | 22.1 | 18.6 | 11.9 |
| 3 | 24.6 | 22.9 | 17.0 | 24.8 | 22.0 | 13.9 | 23.3 | 20.0 | 13.1 |
| 5 | 25.2 | 23.2 | 17.5 | 25.3 | 22.9 | 13.8 | 23.2 | 19.9 | 13.3 |

*Met = Methionine

EXAMPLE 8

Stable nisin formulations useful as topical germicides were prepared at pH 3.5 and set to incubate at 40° C. After 2, 4, and 6 months samples were analyzed by RPHPLC. At 6 months the samples were also analyzed for activity in the MIC assay. The RPHPLC and MIC assay data are presented in Table 14.

TABLE 14

Nisin concentration and MIC (µg/ml) after 6 months at pH 3.5, 40° C.

| EDTA 1 mM | citrate % | T-MAZ 20 1% | Met 1 mM | MIC µg/ml | nisin conc.* µg/ml |
|---|---|---|---|---|---|
| + | | | | 12.5 | 17.8 |
| + | | | + | 12.5 | 22.2 |
| + | | + | | >50 | 11.5 |
| + | | + | + | 12.5 | 19.8 |
| | 0.1 | | | 12.5 | 13.1 |
| | 0.1 | | + | 12.5 | 18.1 |
| | 0.1 | + | | >50 | 3.0 |
| | 0.1 | + | + | 6.25 | 15.8 |
| | 0.3 | | | 12.5 | 13.6 |
| | 0.3 | | + | 12.5 | 15.3 |
| | 0.3 | + | | >50 | 4.1 |
| | 0.3 | + | + | 3.125 | 14.8 |
| | 1.0 | | | 25 | 7.7 |
| | 1.0 | | + | 12.5 | 10.0 |
| | 1.0 | + | | 12.5 | 2.5 |
| | 1.0 | + | + | 6.25 | 9.0 |

*Initial nisin concentration was 25 µg/ml.

We claim:

1. A lanthionine-containing bacteriocin composition stabilized against degradation comprising a lanthionine-containing bacteriocin and a thioether compound of the formula II wherein $R^1$ is an alkyl group containing 1–6 carbon atoms or n is 0–5 wherein R³ is hydrogen or x is 1–3; and
R⁴ is —H, —CH₃, —CH(CH₃)₂, —CH₂CH(CH₃)₂, —CH(CH₃)CH₂CH₃, —CH₂SH, —CH₂CH₂SCH₃, —CH₂OH, —CH(OH)CH₃, —CH₂COOH, —(CH₂)₂COOH, —CH₂CONH₂, —(CH₂)₂CONH₂, —(CH₂)₄NH₂, or —(CH₂)₃— joined with the nitrogen of R³ to form a pyrrolidine ring;
R² is wherein R⁵ is hydrogen, an amino group or a hydroxyl group and R⁶ is hydrogen or wherein R⁷ is hydroxy, alkoxy containing 1–6 carbons atoms or and n, x and R⁴ are as defined above,
with the proviso that if R³ is hydrogen, or if R⁵ is an amino or hydroxyl group, then n is not zero;
and wherein the compound defined by Formula II is methionine, an analog thereof or a peptide containing methionine or methionine analog residues.

2. The composition of claim 1 which further comprises a surfactant.

3. The composition of claim 2 wherein the surfactant is a polysorbate.

4. The composition of claim 1 which further comprises a chelating agent selected from the group consisting of EDTA, CaEDTA, CaNa₂EDTA, EGTA, CDTA, DTPA, HEEDTA, EDITEMPA and citrate.

5. The composition of claim 4 wherein the chelating agent is EDTA or citrate.

6. The composition of claim 1 wherein the bacteriocin is nisin.

7. The composition of claim 1 wherein the compound of formula II is methionine.

8. The composition of claim 7 wherein the concentration of methionine is in the range of 1 to 50 mM.

9. The composition of claim 8 wherein the concentration of methionine is in the range of 1 to 10 mM.

10. The composition of claim 1 wherein R¹ is —CH₃ and R² is —(CH₂)₂—CH(OH)—COOH.

11. A lanthionine-containing bacteriocin composition, stabilized against degradation, comprising the bacteriocin in a concentration range of 0.1 to 1000 μg/ml; a surfactant in a concentration range of 0.1–10%; a chelating agent selected from the group consisting of EDTA, CaEDTA, CaNa₂EDTA, EGTA, CDTA, DTPA, HEEDTA, EDITEMPA and citrate in a concentration range of 0.1–20 mM; and a thioether stabilizing agent according to claim 1 in a concentration range of 1 mM to 10 mM.

12. The composition of claim 1 which further comprises a chelating agent that is an alkylenediamine tetraacetate.

13. A lanthionine-containing bacteriocin composition, stabilized against degradation, comprising the bacteriocin in a concentration range of 0.1 to 1000 μg/ml; a surfactant in a concentration range of 0.1–10%; a chelating agent that is an alkylenediamine tetraacetate in a concentrate of 0.1–20 mM; and a thioether stabilizing agent according to claim 1 in a concentration range of 1 mM to 10 mM.

14. The composition of claim 11 or 13 wherein the bacteriocin is nisin and the stabilizing agent is methionine.

15. A method for stabilizing a lanthionine-containing bacteriocin component of a composition against degradation comprising adding to said composition a compound according to claim 1 in an amount effective to achieve stabilization of said bacteriocin.

* * * * *

UNITED STATES PATENT AND TRADEMARK OFFICE
CERTIFICATE OF CORRECTION

PATENT NO. : 5,763,395
DATED : June 9, 1998
INVENTOR(S) : Blackburn et al.

It is certified that error appears in the above-identified patent and that said Letters Patent is hereby corrected as shown below:

Col. 15, lines 47-51, change the formula

Col. 16, line 43, change "concentrate" to --concentration range--.

Signed and Sealed this

Thirty-first Day of August, 1999

Attest:

Q. TODD DICKINSON

Attesting Officer

Acting Commissioner of Patents and Trademarks